US010751640B1

(12) United States Patent
Ferraro et al.

(10) Patent No.: US 10,751,640 B1
(45) Date of Patent: Aug. 25, 2020

(54) CANNABIDIOL ISOLATE PRODUCTION SYSTEMS AND METHODS

(71) Applicant: Heinkel Filtering Systems, Inc., Swedesboro, NJ (US)

(72) Inventors: Alan Ferraro, Swedesboro, NJ (US); Bob Edwards, Swedesboro, NJ (US)

(73) Assignee: Heinkel Filtering Systems, Inc., Swedesboro, NJ (US)

( * ) Notice: Subject to any disclaimer, the term of this patent is extended or adjusted under 35 U.S.C. 154(b) by 0 days.

(21) Appl. No.: 16/668,583

(22) Filed: Oct. 30, 2019

Related U.S. Application Data

(63) Continuation-in-part of application No. 16/668,432, filed on Oct. 30, 2019.

(51) Int. Cl.
| C07C 37/68 | (2006.01) |
| C07C 39/23 | (2006.01) |
| B01D 9/00  | (2006.01) |
| B01D 11/04 | (2006.01) |
| B01D 21/26 | (2006.01) |

(52) U.S. Cl.
CPC ........ B01D 9/0013 (2013.01); B01D 11/0457 (2013.01); B01D 11/0492 (2013.01); B01D 21/262 (2013.01); C07C 37/685 (2013.01)

(58) Field of Classification Search
None
See application file for complete search history.

(56) References Cited

U.S. PATENT DOCUMENTS

| 3,973,984 A | 8/1976 | Hentschel |
| 5,195,939 A | 3/1993 | Gingras |
| 5,591,340 A | 1/1997 | Meikrantz |
| 6,059,712 A | 5/2000 | Corlett |
| 7,384,557 B2 | 6/2008 | Phillips |
| 8,728,215 B2 | 5/2014 | Manning |
| 8,895,078 B2 | 11/2014 | Mueller |
| 8,998,789 B2 | 4/2015 | Toi |
| 9,732,009 B2 | 8/2017 | Raber |
| 9,808,494 B2 | 11/2017 | Barringer |
| 9,950,976 B1 | 4/2018 | Keller |
| 10,406,453 B2 | 9/2019 | Ko |
| 2005/0019438 A1 | 1/2005 | Bourges-Sevenier |

(Continued)

FOREIGN PATENT DOCUMENTS

| CN | 101972715 A | 2/2011 |
| CN | 204111719 U | 1/2015 |

(Continued)

OTHER PUBLICATIONS

Salem (How to crystallize CBD—Make CBD isolate, Published Mar. 13, 2019) (Year: 2019).*

(Continued)

Primary Examiner — Medhanit W Bahta

(57) ABSTRACT

The disclosure includes systems and methods of producing cannabidiol (CBD) isolate. In some embodiments, a method includes dissolving CBD oil in a solvent to thereby form a slurry comprising a CBD isolate and excess solvent. Methods may thereby include separating, via a centrifuge, at least a portion of the CBD isolate from the excess solvent to thereby form a separated batch. Additionally, some embodiments include drying the CBD isolate from the separated batch.

20 Claims, 13 Drawing Sheets

(56) References Cited

U.S. PATENT DOCUMENTS

| | | |
|---|---|---|
| 2011/0003888 A1 | 1/2011 | Kuhrts |
| 2011/0263030 A1 | 10/2011 | Kim |
| 2013/0079531 A1 | 3/2013 | Barringer |
| 2015/0126754 A1 | 5/2015 | Cid |
| 2015/0353865 A1 | 12/2015 | Poon |
| 2017/0080422 A1 | 3/2017 | Maaskant |
| 2017/0106030 A1 | 4/2017 | Aari |
| 2018/0147247 A1 | 5/2018 | Ivanov |

FOREIGN PATENT DOCUMENTS

| | | |
|---|---|---|
| CN | 105535111 A | 5/2016 |
| CN | 106011207 A | 10/2016 |

OTHER PUBLICATIONS

Pahnke, L. "A More Effective and Efficient Approach to Purer Cannabidiol Production Using Centrifugal Partition Chromatography" Apr. 23, 2018 (Year: 2018).*

Delta Separations; Centrifuge Utility Platform; Downloaded on Jan. 8, 2019 from https://www.deltaseparations.com/extraction/.

Rousselet Robatel; Cannabis Refining; Downloaded on Jan. 8, 2019 from http://www.rousselet-robatel.com/applications/cannabis-refining/.

Delta Separations; Delta Separations CUP; Retrieval date Nov. 29, 2018; Downloaded from https://www.youtube.com/watch?v=PfgFh6ksBKs&feature=youtu.be; Prior art at least as of Jun. 19, 2017.

Medium; Cannabis Tech Hardware Wunderkind; Retrieval date Nov. 29, 2018; Downloaded from https://medium.com/@Pustejovsky/cannabis-tech-hardware-wunderkind-56946f744d1c; Prior art at least as of Nov. 8, 2017.

Venture; Marijuana Venture; Journal of Professional Cannabis Growers and Retailers; pp. 1-54; Downloaded on Jan. 31, 2020; Available from Internet <URL: https://www.marijuanaventure.com/tag/extraction/> Prior art at least as of Jan. 16, 2017.

Salem; How to Crystallize CBD—Make CBD Isolate; Downloaded on Jan. 31, 2020; Available from Internet <URL: http://brinstrument.com/blog/cannabis-distillation/how-to-crystallize-cbd-make-cbd-isolate/>; Prior art at least as of Mar. 13, 2019.

* cited by examiner

CANNABIDIOL ISOLATE PRODUCTION SYSTEMS AND METHODS

BACKGROUND

Field

Various embodiments disclosed herein relate to systems and methods for the continuous production of cannabidiol (CBD) isolate.

Description of Related Art

The production of isolated materials through a crystallization process is a common practice in various fields, particularly in the chemical arts and the pharmaceutical industry. Crystallization is the solidification of atoms or molecules into a highly structured form called a crystal. Usually, this refers to the slow precipitation of crystals from a solution of a substance. However, crystals can form from a pure melt or directly from deposition from the gas phase. Crystallization can also refer to the solid-liquid separation and purification technique in which mass transfer occurs from the liquid solution to a pure solid crystalline phase.

Although crystallization may occur during precipitation, the two terms are not interchangeable. Precipitation simply refers to the formation of an insoluble (solid) from a chemical reaction. A precipitate may be amorphous or crystalline. Other common elements of a crystallization process include at least one temperature change and some form of agitation to assist in the progress of the crystallization process. Different crystallization techniques use a variety of starting materials, including different types of solvents, and varied machinery depending on the type of crystallization taking place.

The production of CBD isolate from CBD oil and a solvent is a relatively new process. Different methods of CBD isolate production use assorted types of complex machinery, including various combinations of reactor tanks, filter dryers, centrifuges, and dryers to collect CBD in a relatively pure form. CBD is a popular compound due to its multitude of health benefits, including pain relief, appetite stimulation, and muscle spasm suppression, among others. Due to the ever increasing demand for CBD and CBD-related products, there is a growing need for efficient and effective ways to produce CBD isolate from CBD oil.

SUMMARY

This disclosure includes methods for CBD isolate production. Some embodiments include a method of producing CBD isolate comprising dissolving, via a first agitated vessel, a first CBD oil in a first solvent to thereby form a first slurry comprising a first CBD isolate and a first excess solvent, sending at least a portion of the first slurry from the first agitated vessel to a centrifuge, separating, via the centrifuge, at least a first portion of the first CBD isolate from the first excess solvent to thereby form a first separated batch, sending at least a portion of the first separated batch to a first dryer, and drying, via the first dryer, at least a second portion of the first CBD isolate from the at least the portion of the first separated batch.

In some embodiments, the first agitated vessel comprises a jacket. The method may further comprise heating, via the jacket of the first agitated vessel, the slurry to reach a dissolving temperature whereby the first CBD oil dissolves in the first solvent. In some embodiments, the method further comprises cooling, via the jacket of the first agitated vessel, the slurry to reach a crystallization temperature whereby CBD crystals precipitate. The method may further comprise agitating, via the first agitated vessel, the first slurry.

The first solvent may comprise at least one of pentane and heptane. In some embodiments, the centrifuge comprises at least one of a filtering centrifuge and a solid bowl centrifuge. The method may further comprise washing the at least the first portion of the first CBD isolate with a wash solvent, wherein the washing occurs at least partially during the separating. In some embodiments, the method further comprises after the washing, collecting excess wash solvent and after the washing, drying, via the first dryer, the at least the first portion of the first CBD isolate. The method may further comprise collecting the at least the first portion of the first CBD isolate in a first collection vessel coupled to the first dryer.

In some embodiments, the method further comprises dissolving, via the first agitated vessel, a second CBD oil in a second solvent to thereby form a second slurry comprising a second CBD isolate and a second excess solvent, after the separating, sending at least a portion of the second slurry from the first agitated vessel to the centrifuge, then, separating, via the centrifuge, at least a first portion of the second CBD isolate from the second excess solvent to thereby form a second separated batch, then, sending at least a portion of the second separated batch to the first dryer, and then drying, via the first dryer, at least a second portion of the second CBD isolate from the at least the portion of the second separated batch.

The method may further comprise dissolving, via a second agitated vessel, a second CBD oil in a second solvent to thereby form a second slurry comprising a second CBD isolate and a second excess solvent, after the separating, sending at least a portion of the second slurry from the second agitated vessel to the centrifuge, then, separating, via the centrifuge, at least a first portion of the second CBD isolate from the second excess solvent to thereby form a second separated batch, then, sending at least a portion of the second separated batch to a second dryer, and then drying, via the second dryer, at least a second portion of the second CBD isolate from the at least the portion of the second separated batch. In some embodiments, the first drying occurs at least partially during the second dissolving and the second separating.

The method may further comprise dissolving, via a second agitated vessel, a second CBD oil in a second solvent to thereby form a second slurry comprising a second CBD isolate and a second excess solvent, after the separating, sending at least a portion of the second slurry from the second agitated vessel to the centrifuge, then, separating, via the centrifuge, at least a first portion of the second CBD isolate from the second excess solvent to thereby form a second separated batch, then, sending at least a portion of the second separated batch to a second dryer, and then drying, via the second dryer, at least a second portion of the second CBD isolate from the at least the portion of the second separated batch. In some embodiments, the first drying occurs at least partially during the second dissolving and the second separating. In some embodiments, the first drying occurs at least partially during the third sending.

In some embodiments, the method further comprises dissolving, via the first agitated vessel, a third CBD oil in a third solvent to thereby form a third slurry comprising a third CBD isolate and a third excess solvent, after the second separating, sending at least a portion of the third slurry from the first agitated vessel to the centrifuge, then, separating, via the centrifuge, at least a first portion of the third CBD isolate from the third excess solvent to thereby form a third separated batch, then, sending at least a portion of the third separated batch to the second dryer, and then drying, via the second dryer, at least a second portion of the third CBD isolate from the at least the portion of the third separated batch. In some embodiments, the third dissolving occurs at least partially during the second drying.

The method may further comprise dissolving, via a third agitated vessel, a third CBD oil in a third solvent to thereby form a third slurry comprising a third CBD isolate and a third excess solvent, after the second separating, sending at least a portion of the third slurry from the third agitated vessel to the centrifuge, then, separating, via the centrifuge, at least a first portion of the third CBD isolate from the third excess solvent to thereby form a third separated batch, then, sending at least a portion of the third separated batch to the second dryer, and then drying, via the second dryer, at least a second portion of the third CBD isolate from the at least the portion of the third separated batch.

In some embodiments, the method further comprises dissolving, via the first agitated vessel, a third CBD oil in a third solvent to thereby form a third slurry comprising a third CBD isolate and a third excess solvent, after the second separating, sending at least a portion of the third slurry from the first agitated vessel to the centrifuge, then, separating, via the centrifuge, at least a first portion of the third CBD isolate from the third excess solvent to thereby form a third separated batch, then, sending at least a portion of the third separated batch to a third dryer, and then drying, via the third dryer, at least a second portion of the third CBD isolate from the at least the portion of the third separated batch.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. Various components in the drawings may not be drawn to scale.

DETAILED DESCRIPTION

Figure 1:
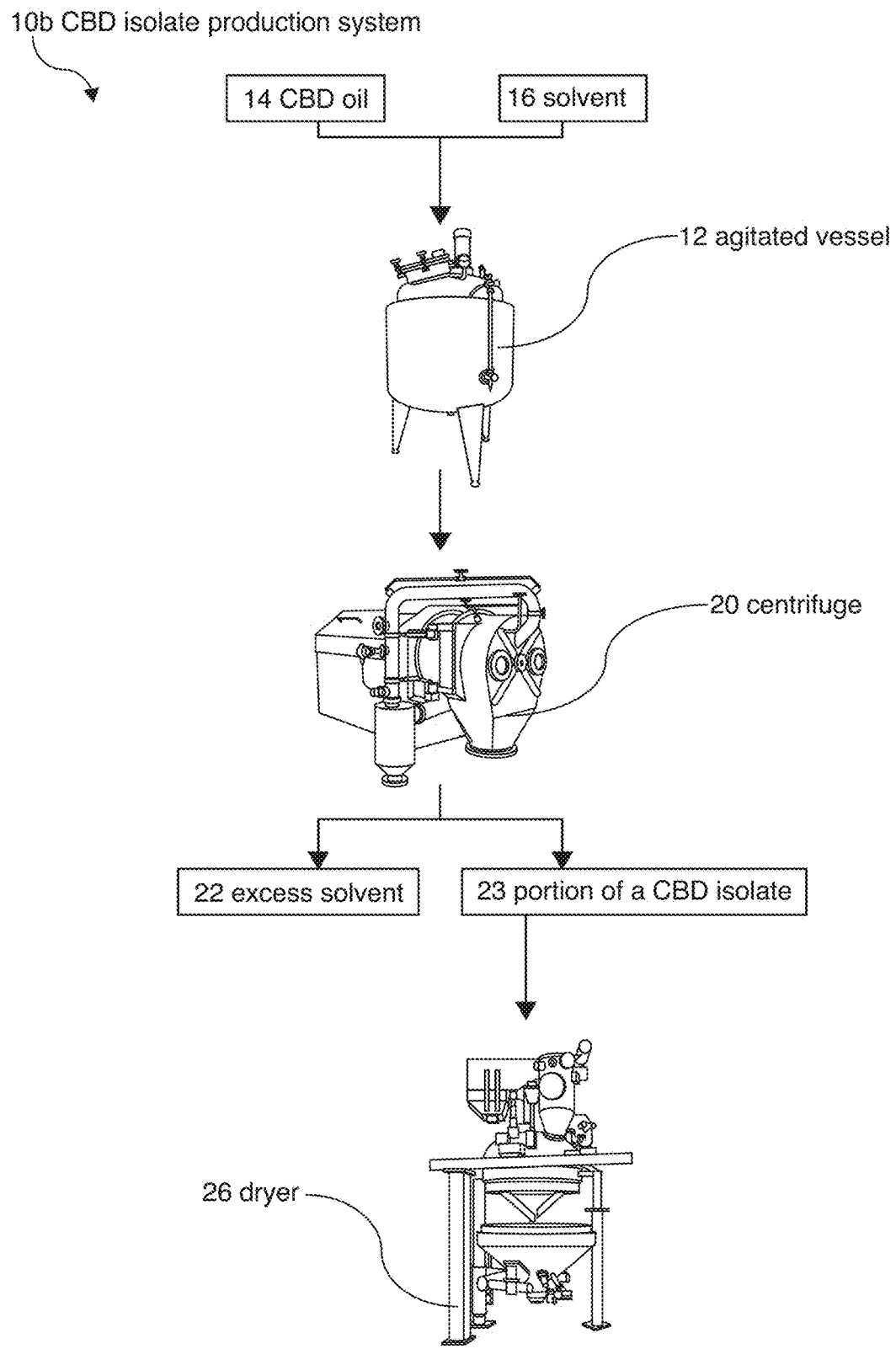
FIG. 1 illustrates a schematic view of a CBD isolate production system, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any system or method disclosed herein, the acts or operations of the system or method may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, methods, and/or procedures described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

INDEX OF COMPONENTS

10—CBD isolate production system
12—agitated vessel
14—CBD oil
16—solvent
18—slurry
20—centrifuge
22—excess solvent
23—portion of a CBD isolate
24—first CBD isolate
26—dryer
28—separated batch
30—collection vessel
32—first wash solvent

INTRODUCTION

Crystallization is the solidification of atoms or molecules into a highly structured form called a crystal. Usually, this refers to the slow precipitation of crystals from a solution of a substance. Agitation, centrifugation, and/or temperature change may be used to assist the reaction in precipitating the desired compound. The solvent and the solid crystals may be separated using a variety of methods, including vacuum filtration, and the solid crystals may undergo further manipulation, such as drying, prior to collection. In some cases, the solvent may be collected for use in a subsequent crystallization processes.

In an example of CBD isolate crystallization process, the process begins with the combination of CBD oil and a solvent, such as pentane, heptane, or other suitable solvent. In some embodiments the CBD oil may be extracted from hemp and/or *cannabis* material by the process described in U.S. patent application Ser. No. 16/286,134 ("the '134 application"); filed on Feb. 26, 2019; and titled "Biomass Extraction and Centrifugation Systems and Methods", which is hereby incorporated by reference.

Following extraction and collection of CBD oil and prior to the crystallization process, the oil may undergo winterization. The winterization process uses freezing and separation to remove waxes and fats from the cannabinoids, thus resulting in an extract of greater purity. The frozen waxes and fats may be separated from the rest of the extract through a manual or an automated process. Following winterization, the CBD oil is ready to be used in the crystallization of CBD isolate crystals.

The CBD isolate production systems and methods of this disclosure implement an automated and continuous process that allows for reduced manual labor, increased efficiency, and improved quantity and quality output. It should be noted that the term "continuous" as used in this disclosure encompasses continuous, semi-continuous, quasi-continuous, and/or batch processing methods. While this disclosure refers primarily to CBD, it is important to realize that the teachings of this disclosure can be implemented across many industries to precipitate any desired components from almost any starting materials.

Referring now to the Figures, FIG. 1 illustrates a schematic view and gives a general idea of the path of materials as they move through the CBD isolate production process of a CBD isolate production system 10a. In some embodiments, the system 10a comprises an agitated vessel 12 and a centrifuge 20. In many embodiments, the agitated vessel 12 and the centrifuge 20 are fluidly coupled. The agitated vessel 12 may receive CBD oil 14 and a solvent 16, and the centrifuge 20 may produce a portion of a CBD isolate 23 and excess solvent 22. The portion of a CBD isolate 23 may then be sent to a dryer 26, which may be fluidly coupled to the centrifuge 20. The fluid coupling of the components in the system 10a may create a closed system capable of continuously receiving CBD oil 14 and solvent 16 and processing the ingredients to yield CBD isolate 23 and excess solvent 22.

The solvent 16 may be at least one of pentane, heptane, and/or any other suitable solvent. It should be noted that the centrifuge 20 may be a filtering centrifuge, such as a Heinkel HF inverting filter centrifuge (sold by Heinkel Process Technology GmbH having an office in Besigheim, Germany). In some embodiments, the centrifuge 20 is a solid bowl centrifuge. The dryer 26 may be at least one of a Comber vacuum dryer (sold by Comber Process Technology S.r.l. having an office in Agrate Brianza, Monza e Brianza, Italy) and a Bolz vacuum dryer (sold by Bolz Process Technology GmbH having an office in Wangen im Allgau, Germany). Other vacuum dryers may also be utilized to assist in the production of CBD isolate. Methods of producing the CBD isolate 24 and excess solvent 22 from the CBD oil 14 and solvent 16 will be discussed in detail with reference to FIGS. 2A, 2B, 2C, 3A, 3B, and 4.

Figure 2A:
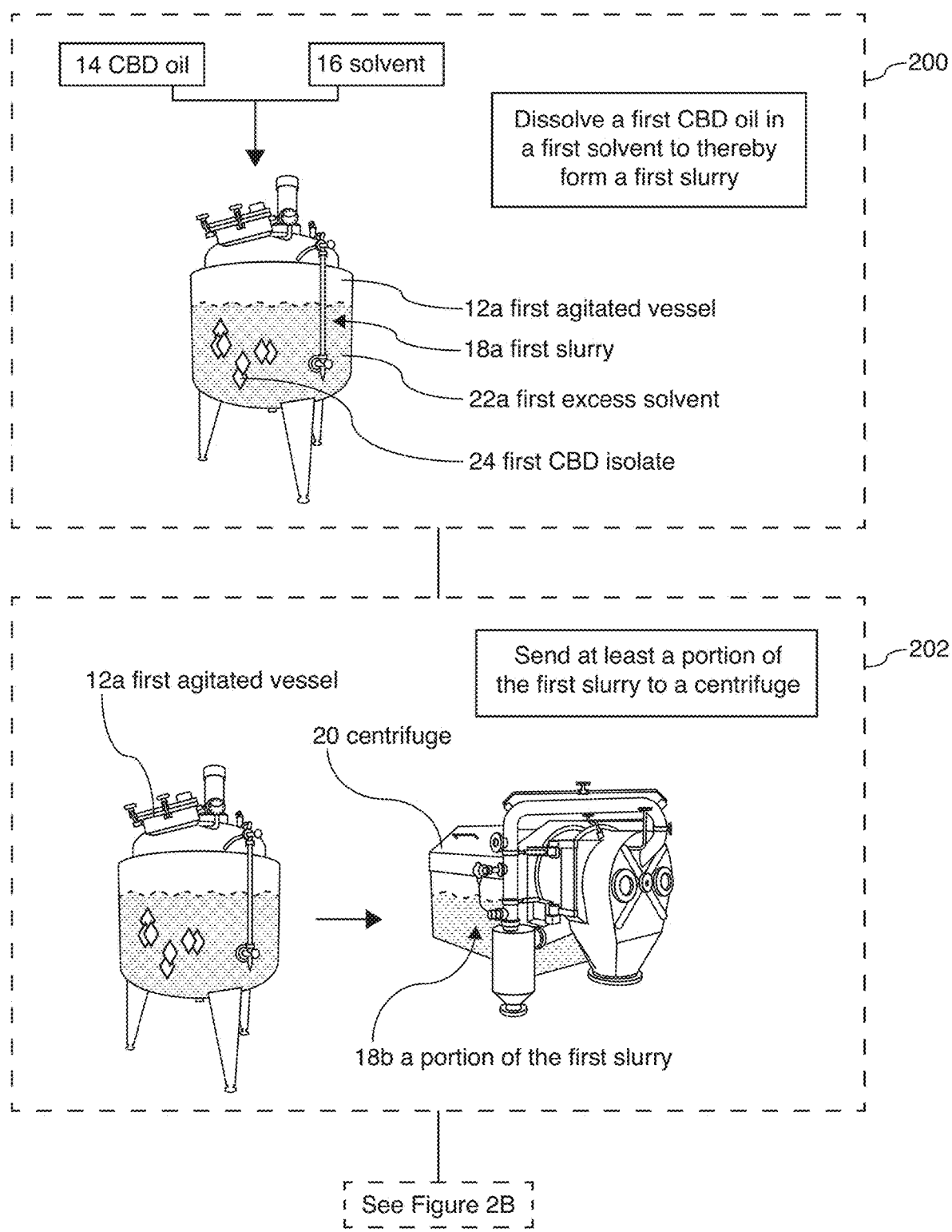
FIGS. 2A, 2B, and 2C illustrate a method of producing CBD isolate, according to some embodiments.
Figure 2B:
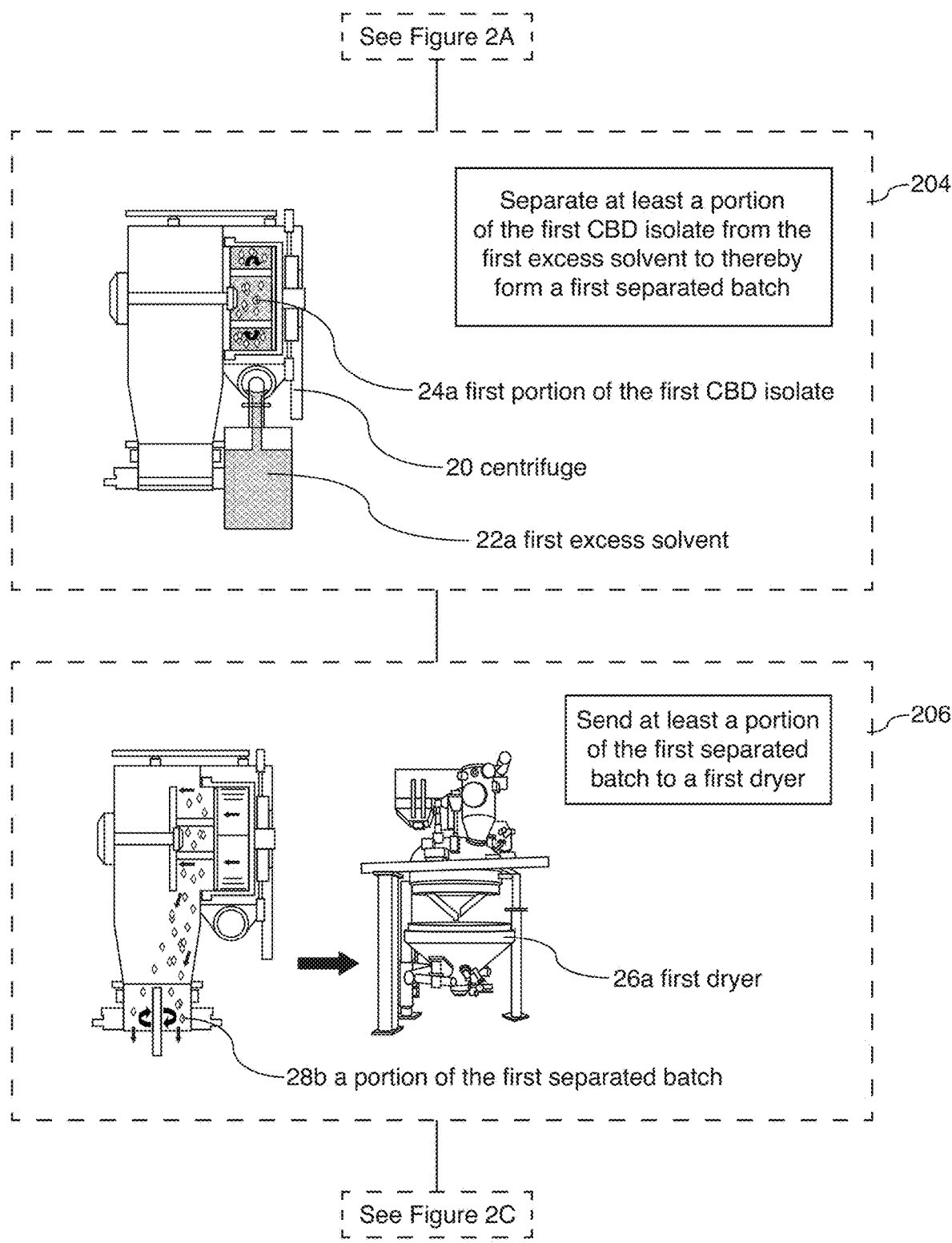
Figure 2C:
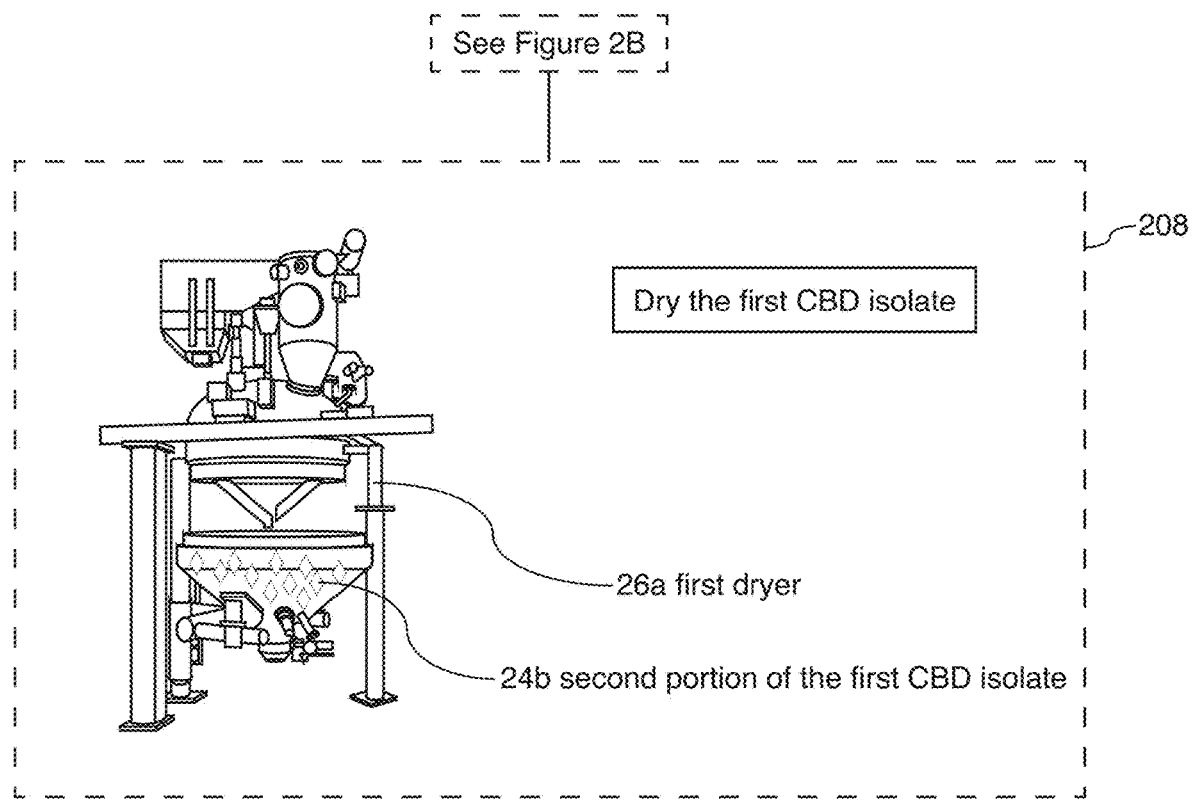

FIGS. 2A, 2B, and 2C illustrate a method of producing CBD isolate, according to some embodiments. As shown in FIG. 2A at step 200, the method may comprise dissolving, via a first agitated vessel 12a, a first CBD oil 14a in a first solvent 16a to thereby form a first slurry 18a comprising a first CBD isolate 24 and a first excess solvent 22a. For purposes of this disclosure, the terms "slurry" and "solution" may be used interchangeably. However, the respective terms may be used to represent specific situations whereby a "solution" is formed upon dissolving of CBD oil 14 in the solvent 16, and whereby a "slurry" is then formed once CBD isolate crystals 24 precipitate out of the "solution."

In some embodiments, discharging the first CBD oil 14a and the first solvent 16a into the first agitated vessel 12a takes between about 15 and 30 minutes. The discharging may take more or less time, depending on the quantity of the first CBD oil 14a and the first solvent 16a being discharged into the first agitated vessel 12a.

The first slurry 18a may comprise a specific ratio of first CBD oil 14a to first solvent 16a. The amount and ratio of first CBD oil 14a to first solvent 16a input into the system 10a may depend on the type, as well as the particular physical and chemical properties of both the first CBD oil 14a and the first solvent 16a used in the system 10a. In several embodiments, the ratio of the first CBD oil 14a to the first solvent 16a is substantially constant to ensure a repeatable process, as well as a consistent and repeatable crystallization result. The repeatable and consistent nature of the ratio of the first CBD oil 14a to the first solvent 16a and the crystallization result may contribute to the continuous manner in which the method operates.

Figure 10:
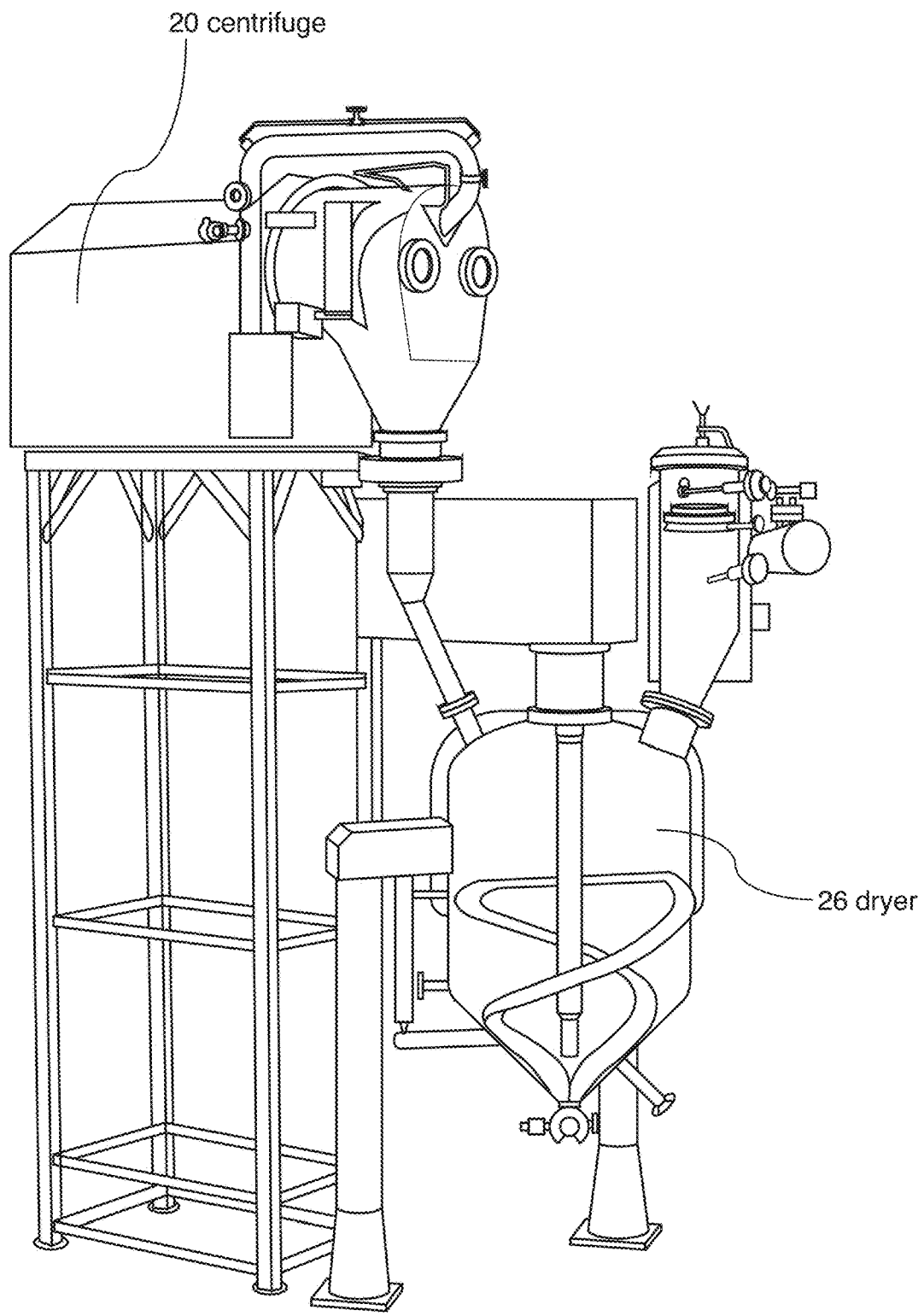
FIG. 10 illustrates a schematic view of a centrifuge and a dryer, according to some embodiments.

According to step 202, the method may further comprise sending at least a portion of the first slurry 18b from the first agitated vessel 12a to a centrifuge 20. In some embodiments, at least a portion of the first slurry 18b is sent to the centrifuge 20 via a fluid coupling mechanism comprising at least one tube, pipe, or the like. The fluid coupling mechanism may be coupled to at least one pump to facilitate the sending. A portion of the first slurry 18a may be loaded into the centrifuge 20 about every 10 minutes on a continuous basis, until the first slurry 18a is depleted. In some embodiments (and as shown in FIG. 10), the first agitated vessel 12a is elevated and the system 10a uses gravity to transfer the at least a portion of the first slurry 18b through the fluid coupling mechanism to the centrifuge 20.

As illustrated in FIG. 2B at step 204, in some embodiments, the method further comprises separating, via the centrifuge 20, at least a first portion of the first CBD isolate 24a from the first excess solvent 22a to thereby form a first separated batch 28a. In some embodiments, the first excess solvent 22a is released throughout the duration of operation of the centrifuge, and the at least a first portion of the first CBD isolate 24a is released once the centrifuge stops spinning. The separating step 204 may take about 10 minutes. The exact time for completion of the separating step 204 depends on a number of factors, including the amount of the at least a portion of the first slurry 18b in the centrifuge 20, the speed of the centrifuge 20, and the type of first solvent 16a. In some embodiments, the centrifuge 20 comprises an HF300.1 inverting filter centrifuge (sold by Heinkel Process Technology GmbH having an office in Besigheim, Germany) and can discharge about 6.5 liters of a first portion of the first CBD isolate 24a every 10 minutes. The centrifuge 20 may comprise an HF600.1 (also sold by Heinkel Process Technology GmbH) inverting filter centrifuge and may discharge about 52 liters of a first portion of the first CBD isolate 24a every 10 minutes. In some embodiments, the centrifuge 20 operates at about 2300 RPM. A centrifuge 20 other than an HF inverting filter centrifuge may have a similar run time of about 10 minutes.

The method may further comprise sending at least a portion of the first separated batch 28b to a first dryer 26a (at step 206). In an embodiment where the centrifuge 20 comprises an HF inverting filter centrifuge, the at least a portion of the first separated batch 28b may be removed from the centrifuge 20 by inverting the filter of the HF inverting filter centrifuge. Inverting the filter may provide a gentle release of the at least a portion of the first separated batch 28b, and may increase efficiency of the system 10a by not requiring human intervention to empty the centrifuge 20. In many embodiments, the at least the portion of the first separated batch 28b comprises at least a first portion of the first CBD isolate 24a. The first excess solvent 22a may be collected from the centrifuge 20 for use in a subsequent round of producing CBD isolate. FIG. 2C continues with step 208, which demonstrates drying, via the first dryer 26a, at least a second portion of the first CBD isolate 24b.

In some embodiments, the drying comprises a thermal process to remove residual solvent 16a from the portion of the first separated batch 28b. The drying may further comprise applying a vacuum to the internal portion of the first dryer 26a. In this regard, the drying may occur in response to applying the vacuum. Applying the vacuum may allow the portion of the first separated batch 28b to dry at a lower temperature than would likely be needed without the vacuum. In some embodiments, the vacuum is achieved by applying a vacuum via the first dryer 26a. The vacuum may be applied using an external component coupled to the first dryer 26a. In many embodiments, the centrifuge 20 mechanically removes most of the first solvent 16a as the first excess solvent 22a, leaving behind only residual solvent 16a in the first portion of the first CBD isolate 24a. In some embodiments, the drying step 208 further comprises agitating. The agitation process may include stirring and/or mixing the at least a second portion of the first CBD isolate 24b within the first dryer 26a and/or any other suitable form of agitation. Some forms of agitation, such as stirring and/or mixing, may be achieved through the use of an agitator within the first dryer 26a. In many embodiments, the drying step 208 takes between about 1 and 2 hours. The drying time could be more or less, depending on the quantity of the portion of the first separated batch 28b, as well as the amount of moisture in the portion of the first separated batch 28b.

Figure 3A:
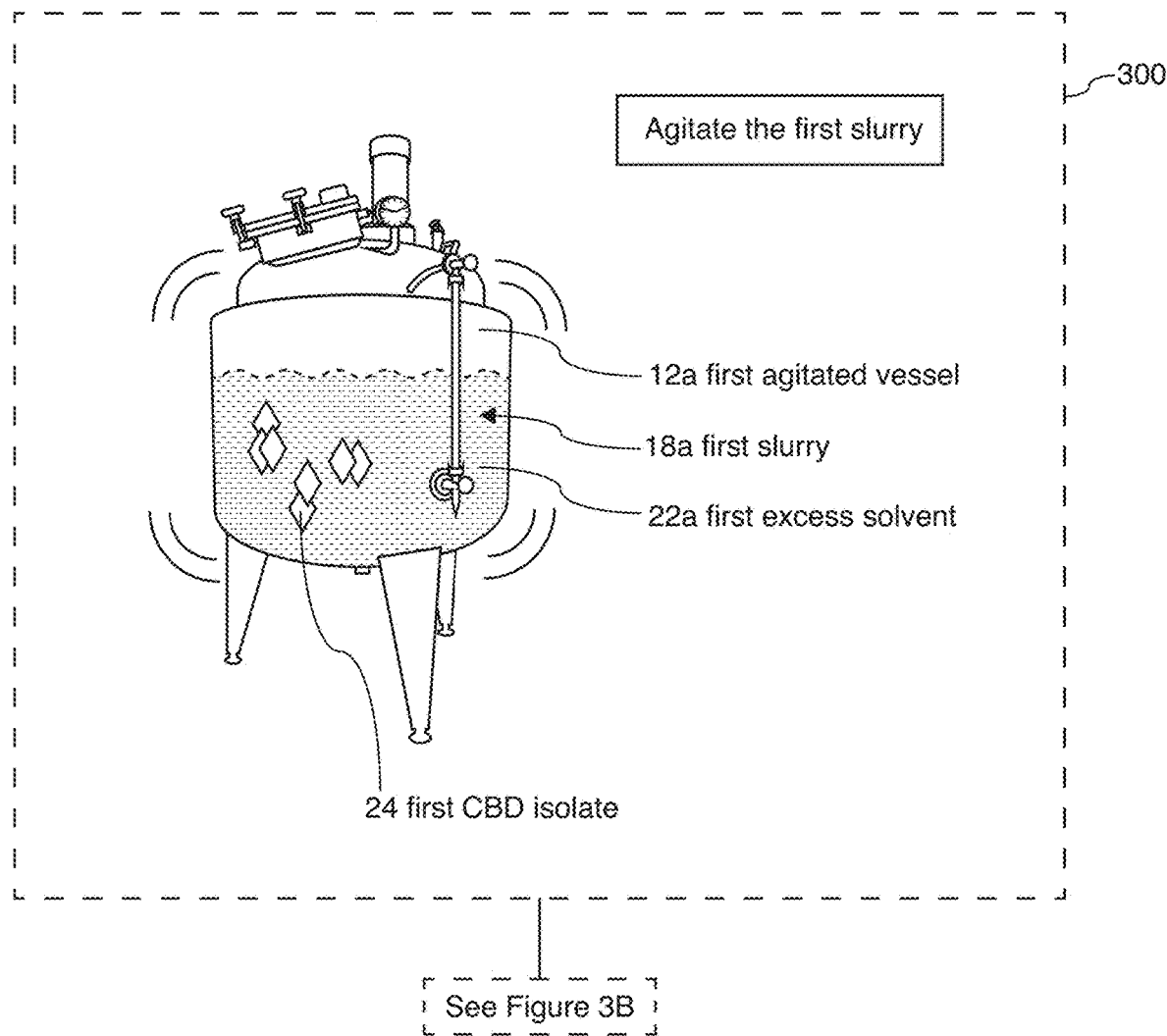
FIGS. 3A and 3B illustrate a method of producing CBD isolate, according to some embodiments.
Figure 3B:
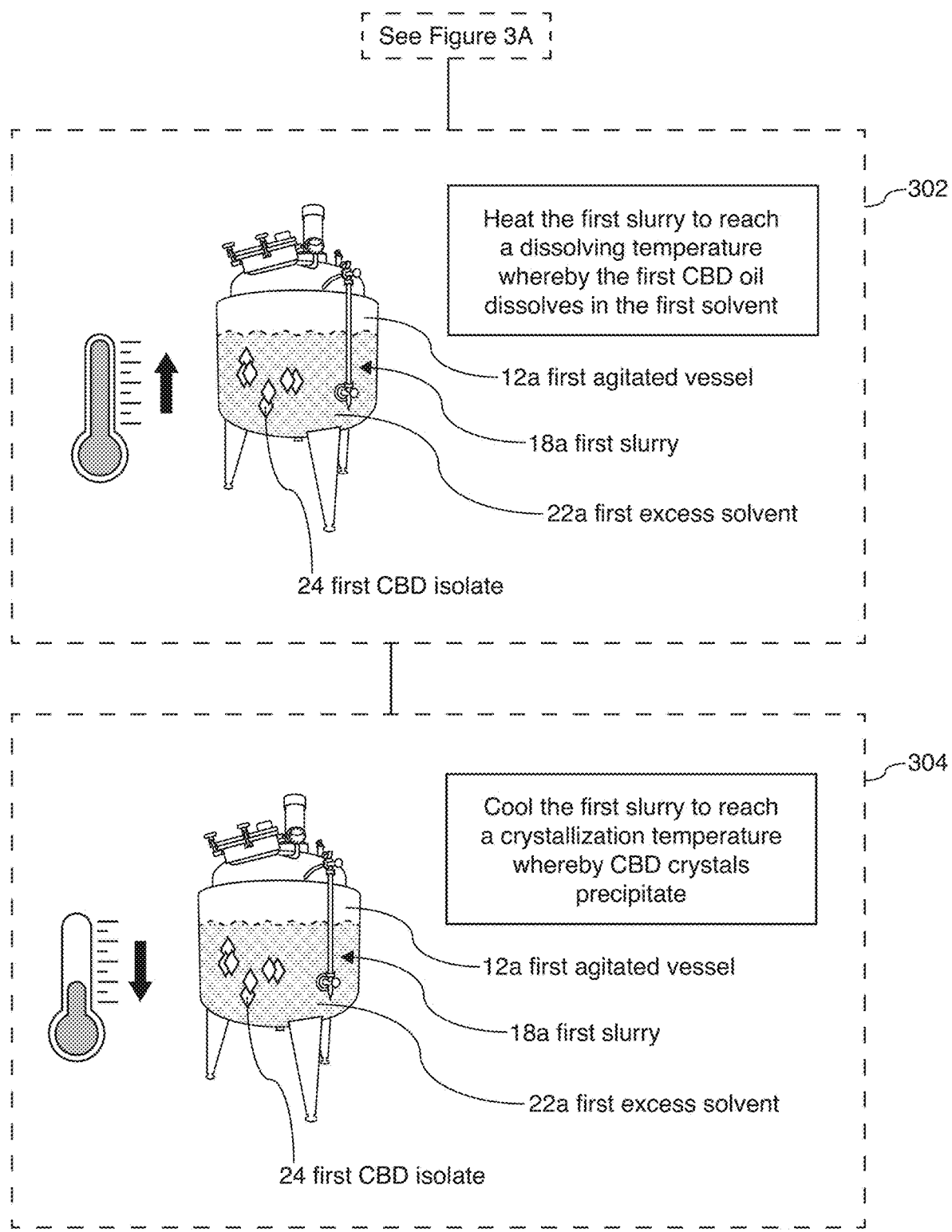

FIGS. 3A and 3B show a method of producing CBD isolate, according to some embodiments. Step 300 of FIG. 3A illustrates agitating, via the first agitated vessel 12a, the first slurry 18a. As mentioned previously in this disclosure, agitation may be used to facilitate the formation of crystals in a crystallization process. In some embodiments, agitation is not necessary to successfully precipitate a first CBD isolate 24. The agitation may work continuously for constant mixing or may operate intermittently for periods of mixing and rest, as appropriate. In some embodiments, the agitating may occur after the dissolving illustrated in FIG. 2A at step 200.

In some embodiments, the first agitated vessel 12a comprises a jacket. FIG. 3B shows that the jacket may be used to alter the temperature of the first agitated vessel 12a, and therefore the temperature of the contents within the first agitated vessel 12a. The change in temperature may be facilitated by liquid heating and/or cooling within the jacket, electric heating and/or cooling of the jacket, and any other appropriate methods. Other appropriate methods of heating and/or cooling may include at least partially immersing a hot or cold coil in the first slurry 18a and using an external heat exchanger to facilitate heating and/or cooling of the first slurry 18a.

Step 302 shows heating a jacket of the agitated vessel 12 to thereby heat at least a portion of an internal portion of the first agitated vessel 12a to reach a dissolving temperature whereby the first CBD oil 14a dissolves in the first solvent 16a. In some embodiments, the dissolving temperature is greater than or equal to about 40 degrees C. The dissolving temperature may vary based on any number of factors in the crystallization process, including the type of first solvent 16a used, the amount of first CBD oil 14a and first solvent 16a used, the presence of impurities in the first CBD oil 14a, and various other factors.

After heating the first slurry 18a to dissolve the first CBD oil 14a, the method may further comprise cooling, via the jacket of the first agitated vessel 12a, the first slurry 18a to reach a crystallization temperature whereby CBD crystals precipitate out of the first slurry 18a, as shown in step 304 of FIG. 3B. In some embodiments, the crystallization temperature is less than or equal to about −10 degrees C. The crystallization temperature may vary based on any number of factors in the crystallization process, including the type of first solvent 16a used, the amount of first CBD oil 14a and first solvent 16a used, the presence of impurities in the first CBD oil 14a, and various other factors. FIGS. 3A and 3B show the presence of a first CBD isolate 24, represented as crystals, inside the first agitated vessel 12a as part of the first slurry 18a. It should be noted that though a crystal shape throughout the Figures represents the CBD isolate 24, the isolate 24 may take other forms. It should also be noted that FIGS. 3A and 3B show the agitating step 300 occurring before the heating step 302 and cooling step 304. In some embodiments, the agitating step 300 may occur at least partially simultaneously with at least one of the heating step 302 and the cooling step 304.

In some embodiments, dissolving the first CBD oil 14a in the first solvent 16a is achieved through the use of a pre-warmed first solvent 16a. Such an embodiment may not require the heating step described in step 302 of FIG. 3B. The first solvent 16a may be warmed in a manner similar to the heating step 302; i.e. through the use of a jacketed vessel containing the first solvent 16a.

In some embodiments, the heating step 302 and cooling step 304 may be followed by sending at least a portion of the first slurry 18b from the first agitated vessel 12a to a centrifuge 20, as illustrated by step 202 in FIG. 2A. The method may further comprise separating, via the centrifuge 20, at least a first portion of the first CBD isolate 24a from the first excess solvent 22a to thereby form a first separated batch 28a, as illustrated in FIG. 2B at step 204. In some embodiments, the method further comprises sending at least a portion of the first separated batch 28b to a first dryer 26a, as illustrated in FIG. 2B at step 206, and drying, via the first dryer 26a, at least a second portion of the first CBD isolate 24b from the at least the portion of the first separated batch 28b, as illustrated by step 208 of FIG. 2C.

Figure 4:
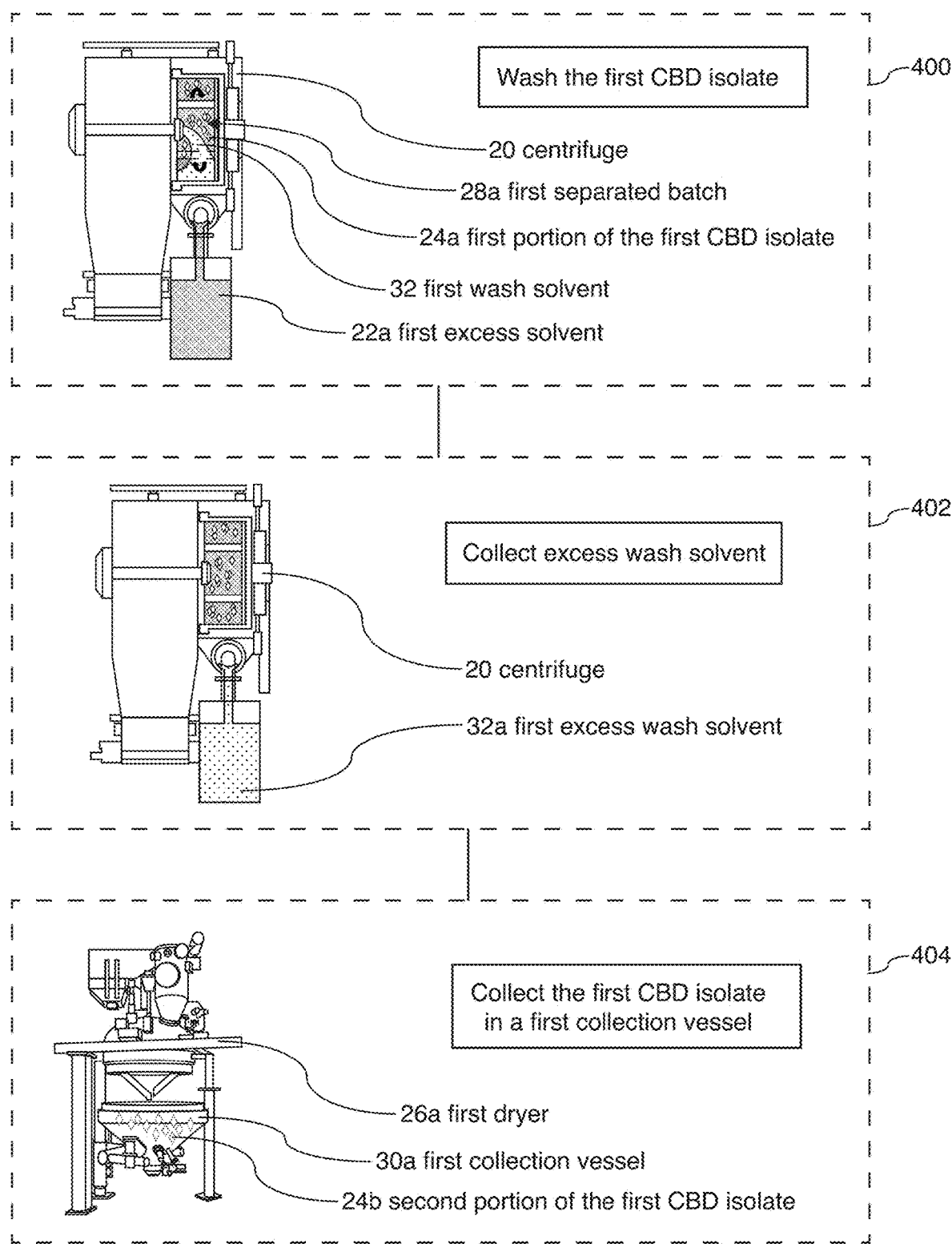
FIG. 4 illustrates a method of producing CBD isolate, according to some embodiments.

As shown in FIG. 4, step 400 illustrates that methods may comprise washing the at least the first portion of the first CBD isolate 24a with a first wash solvent 32. In some embodiments, the washing occurs at least partially during the separating. In many embodiments, the first wash solvent 32 is a cold solvent defining a temperature less than or equal to about −10 degrees C. The first wash solvent 32 may be different than the first solvent 16a used to dissolve the first CBD oil 14a and form the first slurry 18a. Prior to the washing, the first wash solvent 32 may be held in a separate component of the system 10a and added in a manner similar to the sending step described with reference to FIG. 2A at step 202; i.e. through a fluid coupling mechanism. In some embodiments, the washing step 400 facilitates further purification of the first portion of the first CBD isolate 24a by removing residual first excess solvent 22a and any other impurities present in the first portion of the first CBD isolate 24a.

In some embodiments, the washing step 400 occurs after separating, via the centrifuge 20, at least a first portion of the first CBD isolate 24a from the first excess solvent 22a to thereby form a first separated batch 28a, as illustrated by step 204 of FIG. 2B. Prior to the separating, the method may further comprise the dissolving step illustrated in FIG. 2A at step 200 and the sending step illustrated in FIG. 2A at step 202. Following the dissolving but prior to the sending at least a portion of the first slurry 18b from the first agitated vessel 12a to the centrifuge 20, the method may further comprise the agitating, heating, and cooling steps discussed above and illustrated in FIGS. 3A and 3B.

Step 402 of FIG. 4 illustrates that, in some embodiments, the method further comprises collecting a first excess wash solvent 32a. Similar to the first excess solvent 22a collected in step 204 of FIG. 2B, the first excess wash solvent 32a may be collected for use in a subsequent round of producing CBD isolate. In some embodiments, collecting the first excess wash solvent 32a comprises collecting substantially the same quantity of first wash solvent 32 added to the centrifuge 20 in the washing step 400. Following the collecting step 402, the method may further comprise sending at least a portion of the first separated batch 28b to a first dryer 26a, as illustrated by step 206 of FIG. 2B. In some embodiments, the method comprises the drying step illustrated by step 208 of FIG. 2C.

Following the sending and drying steps, some embodiments further comprise step 404: collecting at least the first portion of the first CBD isolate 24a in a first collection vessel 30a coupled to the first dryer 26a. The first collection vessel 30a may be sized and configured to contain CBD isolate from a single round of crystallization or from multiple rounds. In an embodiment where the first collection vessel 30a is configured to contain CBD isolate from multiple rounds of crystallization, the system 10a may run the crystallization process multiple times over a predetermined amount of time and require collection of the isolate from the first collection vessel 30a fewer times than the total number of rounds. For example, the crystallization process may occur multiple times during a shift and the first collection vessel 30a may be emptied just once during the shift. Appropriate sizing of the first collection vessel 30a may increase efficiency of the system 10a and require reduced human intervention.

The method of producing a first CBD isolate 24 illustrated in FIGS. 2A-4 shows an embodiment of the system 10a comprising one agitated vessel 12 and one dryer 26, as shown in FIG. 1. As previously mentioned, this disclosure is directed to a continuous process of producing CBD isolate. Though not shown in FIGS. 2A-4, in some embodiments while the first batch of CBD isolate is in production, a second batch of CBD isolate may also be processed using the system 10a. In this way, the method may allow for a higher production capacity and increased efficiency over the prior art methods of producing CBD isolate.

In some embodiments, a method of producing a second batch of CBD isolate comprises dissolving, via the first agitated vessel, a second CBD oil in a second solvent to thereby form a second slurry comprising a second CBD isolate and a second excess solvent. The second CBD oil and the second solvent may be the same as the first CBD oil 14a and the first solvent 16a. In some embodiments, the second CBD oil and the second solvent may be different from the first CBD oil 14a and the first solvent 16a. Dissolving the second CBD oil in the second solvent may take place while the at least a portion of the first separated batch 28b is being sent from the centrifuge 20 to the first dryer 26a, as shown in step 206 of FIG. 2B.

The method may further comprise sending at least a portion of the second slurry from the first agitated vessel 12a to the centrifuge 20, which may occur after the separating step of the first batch (shown in step 204 of FIG. 2B). In some embodiments, sending at least a portion of the second slurry to the centrifuge 20 occurs at least partially during the drying step of the first batch (step 208 of FIG. 2C).

The method may further comprise separating, via the centrifuge 20, at least a first portion of the second CBD isolate from the second excess solvent to thereby form a second separated batch. In some embodiments, this separating step is substantially similar to the separating steps of the first batch (204 of FIG. 2B). In an embodiment where the first CBD oil 14a and the second CBD oil are the same, and the first solvent 16a and the second solvent are the same, the separating steps for batch one and batch two may take substantially the same amount of time. In an embodiment where the first CBD oil 14a differs from the second CBD oil and/or the first solvent 16a differs from the second solvent, the separating times may be different.

In some embodiments, the method further comprises sending at least a portion of the second separated batch to the first dryer 26a and drying, via the first dryer 26a, at least a second portion of the second CBD isolate from the at least the portion of the second separated batch. In many embodiments, the first dryer 26a is available to dry the second portion of the second CBD isolate because it has completed the drying step for the first batch. A continuous process such as the method described herein may increase efficiency of the system 10a by reducing "down time" of the first dryer 26a; i.e. the time between drying steps for the first and second batch. The system 10a may achieve increased efficiency when the first dryer 26a has less down time between drying steps of the first batch and the second batch, the second batch and a third batch, a third batch and a fourth batch, and so on.

Figure 5:
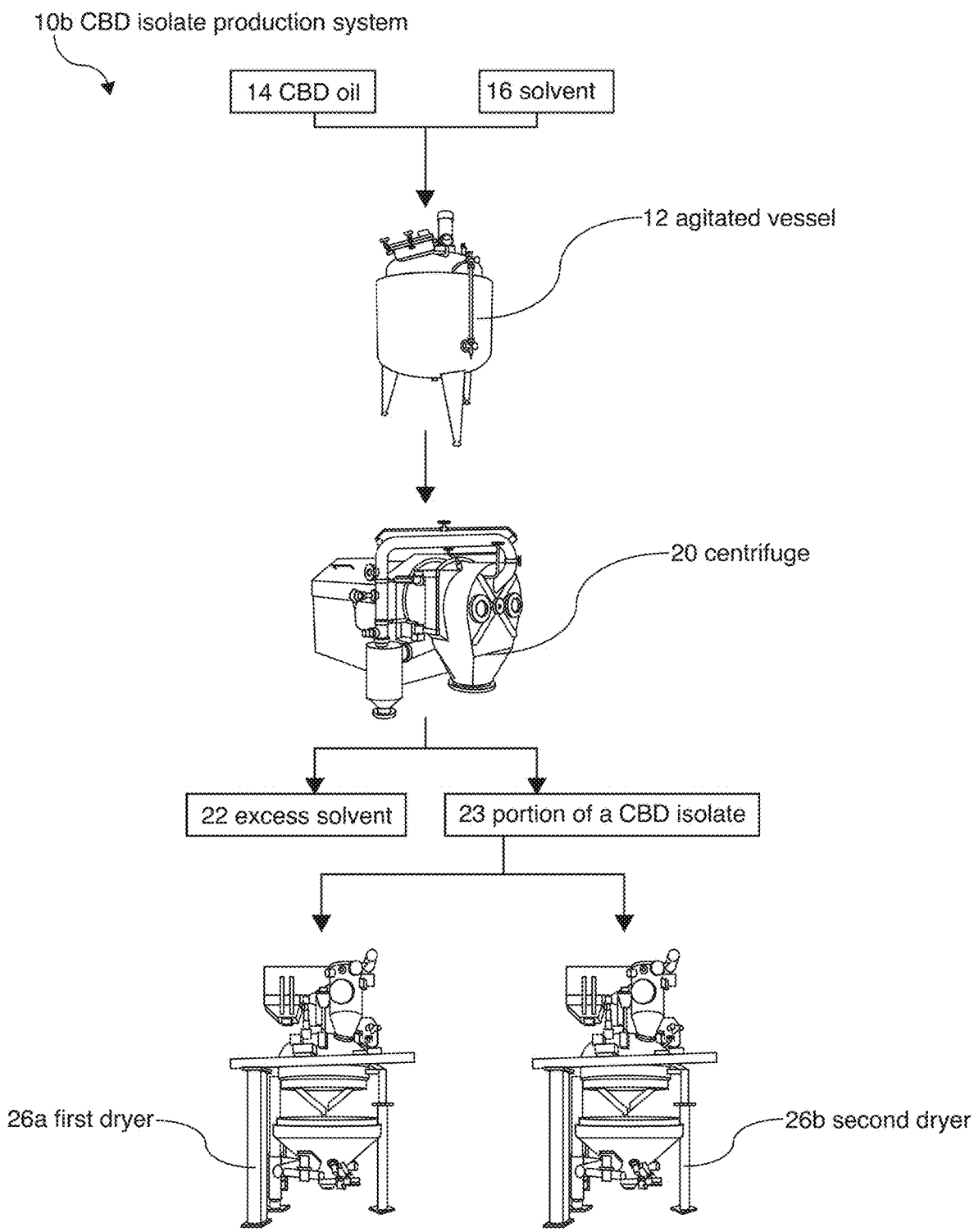
FIG. 5 illustrates a schematic view of a CBD isolate production system, according to some embodiments.

FIG. 5 shows a schematic view of a CBD isolate production system 10b, according to some embodiments. The system 10b is similar to the system 10a (shown in FIG. 1), but in some embodiments, the system 10b includes a first dryer 26a and a second dryer 26b. The addition of the second dryer 26b increases the efficiency of the system 10b because the second batch can be dried in the second dryer 26b, rather than have to wait for the first dryer 26a to be vacant, as with the system 10a. In some embodiments, the centrifuge 20 sends a portion of each batch to the first dryer 26a and the second dryer 26b about every 10 minutes. As such, the system 10b may facilitate the drying of two batches of CBD isolate at least partially at the same time. In some embodiments, the second batch enters the dissolving step while the first batch is in the separating step, which is notably sooner than the embodiment of system 10a that entered the second batch dissolving step when the first batch was being sent from the centrifuge to the dryer. In some embodiments, there is a larger amount of time between the first batch and the second batch, and the first batch drying step occurs at least partially during the second batch dissolving and separating steps. The reduced amount of time between running a first batch and running a second batch may increase the quantity of CBD isolate that is produced over a predetermined amount of time.

Figure 6:
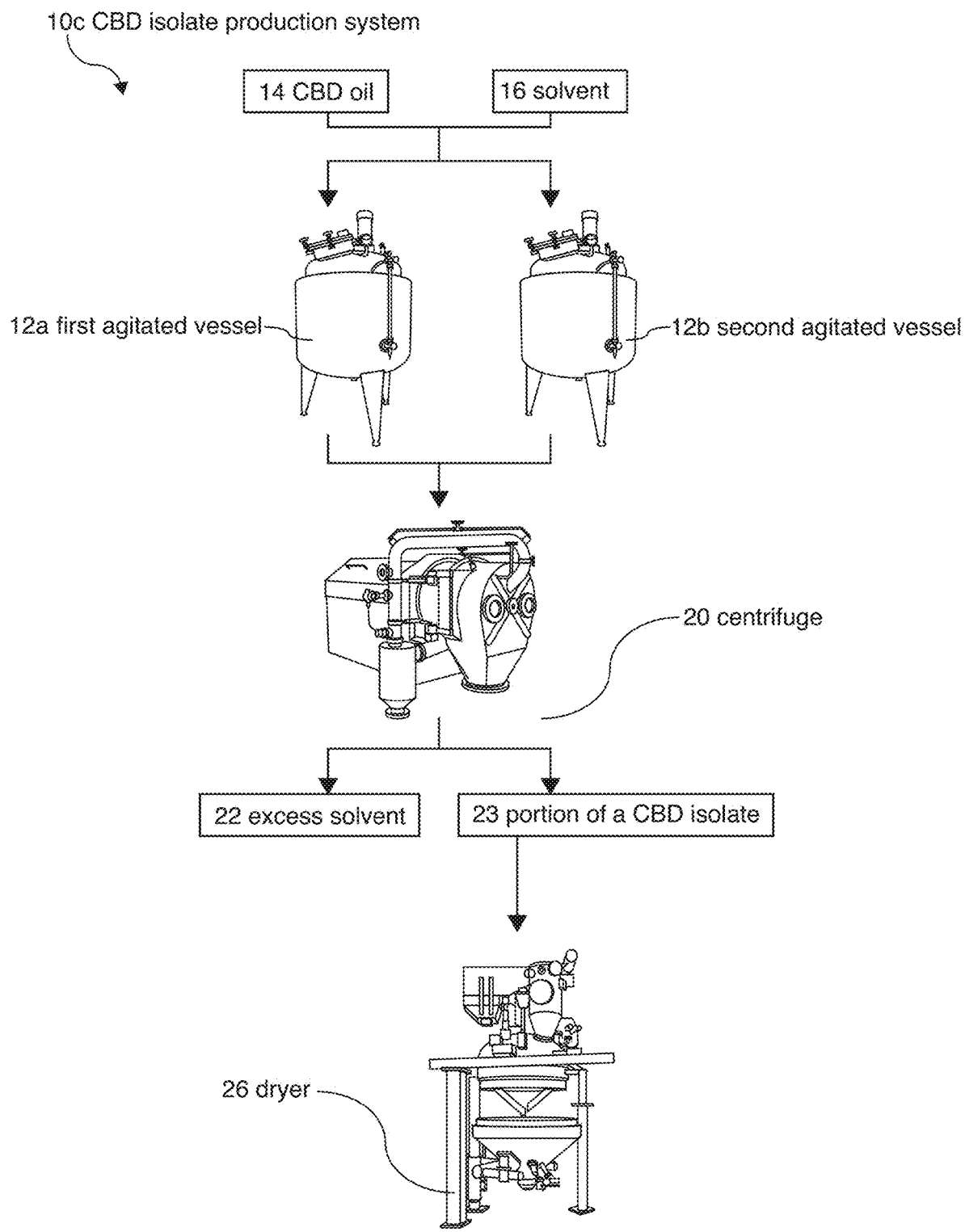
FIG. 6 illustrates a schematic view of a CBD isolate production system, according to some embodiments.

FIG. 6 shows a schematic view of a CBD isolate production system 10c, according to some embodiments. In some embodiments, the system 10c comprises a first agitated vessel 12a and a second agitated vessel 12b, and a single dryer 26. The addition of a second agitated vessel 12b may reduce "down time" of the centrifuge 20 by continuously dissolving (and agitating, heating, and/or cooling) the next batch to be sent to the centrifuge 20. In some embodiments, the first batch dissolving step occurs at least partially during the second batch dissolving and separating steps. In some embodiments, the total crystallization process time and volume are limited by the speed and capacity of the dryer 26. The continuous loading and running of the centrifuge 20 may facilitate continuous loading and use of the dryer 26, leading to highly efficient production of CBD isolate using the system 10c.

Figure 7:
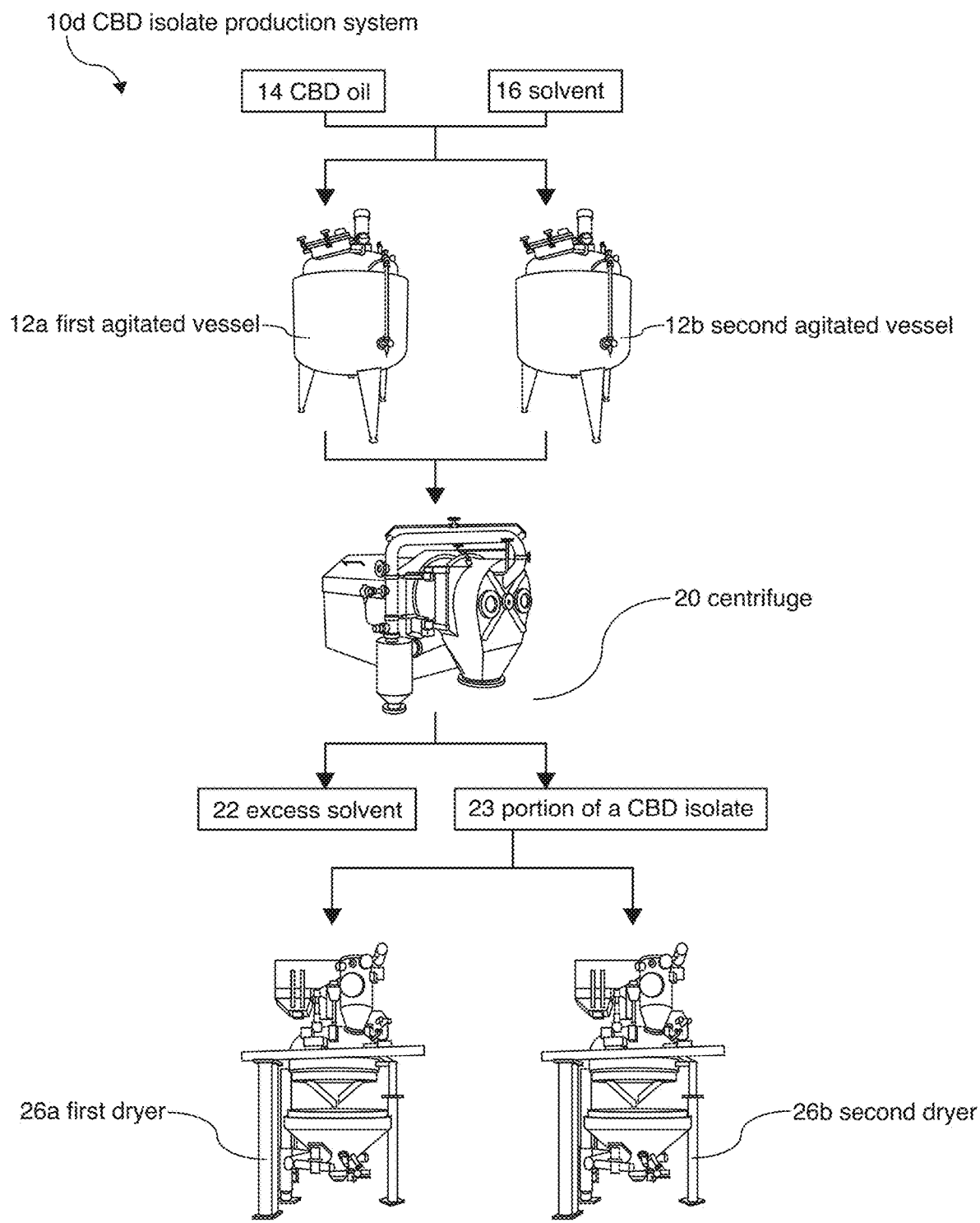
FIG. 7 illustrates a schematic view of a CBD isolate production system, according to some embodiments.

According to FIG. 7, the disclosure also includes yet another CBD isolate production system 10d. The system 10d is similar to the systems 10a-c, however it comprises a first agitated vessel 12a and a second agitated vessel 12b, and a first dryer 26a and a second dryer 26b. In some embodiments, the dissolving steps of a first batch (in the first agitated vessel 12a) and a second batch (in the second agitated vessel 12b) occur at least partially at the same time. In addition, the drying steps of the first batch (in the first dryer 26a) and the second batch (in the second dryer 26b) may occur at least partially at the same time. The system 10d may also accommodate a third batch of a CBD isolate crystallization process, such that in some embodiments, the first batch drying step occurs at least partially during the third batch sending step. The third batch dissolving step may occur at least partially during the second batch drying step. In some embodiments, the process time and production quantity of the system 10d is limited by the speed and capacity of the centrifuge 20. In this and the other systems 10a-c and 10e-f (discussed below), the centrifuge may be sized and configured to accommodate separation of more than one batch (i.e. more than one slurry) at a time. The system 10d may thereby provide increased speed and efficiency in producing CBD isolate.

Figure 8:
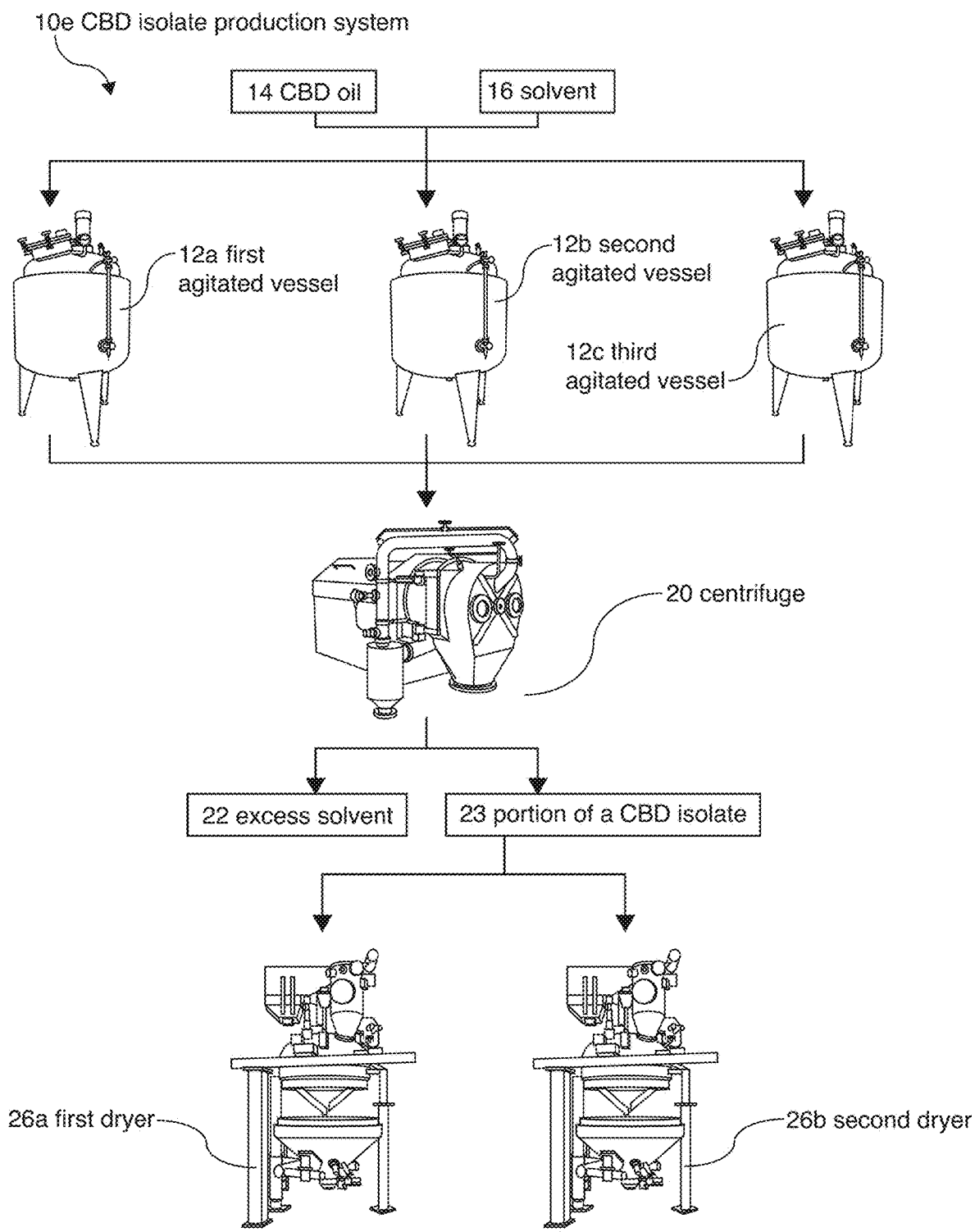
FIG. 8 illustrates a schematic view of a CBD isolate production system, according to some embodiments.

FIG. 8 shows a schematic view of a CBD isolate production system 10e, where the system 10e comprises a first, a second, and a third agitated vessel 12a,b,c, and a first and a second dryer 26a,b, according to some embodiments. The use of three agitated vessels may facilitate dissolving three CBD oils in three solvents at least partially at the same time. The centrifuge 20 of the system 10e may be loaded and run continuously, and may continuously discharge separated batches into at least one of the first dryer 26a and the second dryer 26b.

Figure 9:
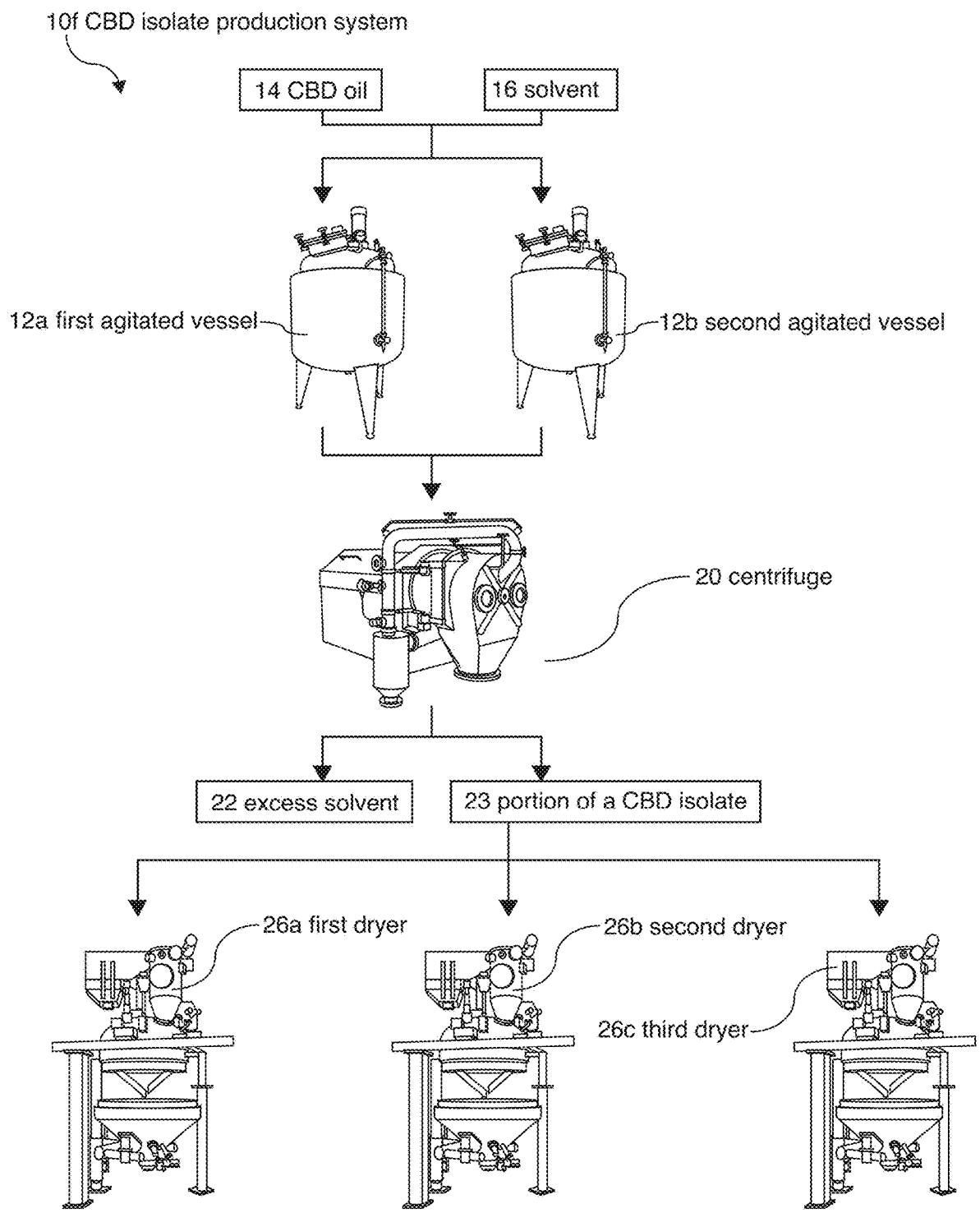
FIG. 9 illustrates a schematic view of a CBD isolate production system, according to some embodiments.

The disclosure includes yet another configuration of the CBD isolate production system 10f. According to FIG. 9, the system 10f comprises a first and second agitated vessel 12a, b, and a first, second, and third dryer, 26a, b, and c. The use of three dryers may facilitate drying three batches of CBD isolate at least partially at the same time. The centrifuge 20 of the system 10f may be loaded and run continuously from the vessels 12a,b, and may continuously discharge separated batches into at least one of the first dryer 26a, the second dryer 26b, and the third dryer 26c.

FIG. 10 illustrates a schematic view of a centrifuge 20 fluidly coupled to a dryer 26. In some embodiments, FIG. 10 demonstrates how gravity, rather than a pump, may be used to send contents from the centrifuge 20 through the fluid coupling mechanism and to the dryer 26. Though not shown, the centrifuge 20 may be configured to be fluidly coupled to a plurality of dryers.

As previously mentioned, the fluid coupling mechanism may create a closed system for the CBD isolate production process. In addition to the fluid coupling mechanism, the systems 10a-f may include additional components for maintaining control over process parameters. For example, at least one of the agitated vessel(s) 12, the centrifuge 20, and the dryer(s) 26 may comprise at least one of a cover(s) to protect the contents of the component and a control valve(s) to regulate the flow of contents between the components. The cover(s) may also aid in temperature regulation as a component of insulation for the agitated vessel(s) 12, the centrifuge 20, and/or the dryer(s) 26. In some embodiments, the cover(s) is attached to at least one of the components with a hinge, allowing the cover(s) to be opened and closed. Alternatively, the cover(s) may be completely removable from at least one of the components. In some embodiments, the cover(s) includes an opening(s), such as a hole(s), to provide a connection(s) to the fluid coupling mechanism in order to facilitate the transfer of contents between components.

In many embodiments, the control valve(s) opens and closes in response to an availability of the centrifuge 20 and/or the dryer 26. The centrifuge 20 may direct the control valve(s) of the one of the components, such as the agitated vessel(s) 12 to open, thus releasing the slurry 18 from the agitated vessel 12 to the centrifuge 20 without manual intervention from a system user. Once the slurry 18 is centrifuged, the centrifuge 20 may immediately indicate an availability and trigger the control valve of the centrifuge 20 to open and release a portion of the separated batch from the centrifuge 20 to the dryer(s) 26, thus allowing the portion of the separated batch to proceed to drying. This feature may allow the system to run in a continuous manner and increase efficiency while reducing the need for manual intervention, as well as decreasing "down time" of the centrifuge 20.

In many embodiments, the agitated vessel(s) 12, the centrifuge 20, and the dryer(s) 26 are sized and configured according to the crystallization process volume. As illustrated by FIGS. 5-9, a plurality of agitated vessels 12 and/or dryers 26 may be used where appropriate for the process volume. Other components of the systems 10a-f including the collection vessel 30, the fluid coupling mechanism, and the quantities of CBD oil 14, solvent 16, and wash solvent 32 may also be sized according to the crystallization process volume. In some embodiments, the dryer(s) 26 are sized to accept several discharge cycles from the centrifuge 20.

Various machinery components of the systems 10a-f, including the agitated vessel(s) 12, the centrifuge 20, the fluid coupling mechanism, the dryer(s) 26, and the collection vessel 30 may comprise any suitable single or combination of materials such as metal, plastic, rubber, and/or glass. The proper material or combination of materials for each component may be determined by the role of the component in crystallizing CBD isolate.

Standard centrifugation uses centrifugal force to facilitate the separation of liquids from solids. Centrifugal force is generated by spinning a sample—in the case of this disclosure, a slurry—at high speed for whatever time is necessary to separate the sample. Hydraulic pressure is created by liquid moving through the cake, and once the liquid is removed there is no more hydraulic pressure. While standard centrifugation is generally very effective, spinning and centrifugal force alone can only remove so much moisture from a sample.

Pressure Added Centrifugation (PAC) introduces pressure force to the centrifugation process in order to remove liquid that might typically be left behind after a standard centrifugation process, as the leftover liquid usually isn't enough to generate its own hydraulic pressure to separate from the sample. In the context, a PAC system may be used to drive additional moisture from the solvent (e.g. pentane or heptane) out of the CBD isolate. This step may be beneficial to remove additional solvent, thus resulting in a CBD isolate of greater purity. The use of PAC may also decrease the drying time of the process by reducing the amount of moisture that goes into the dryer. In some embodiments, the use of PAC eliminates the need for a separate drying cycle, as the PAC system removes substantially all of the residual moisture.

In some embodiments, the centrifuge 20 used to carry out the separating steps 204, 310, 410 comprises a PAC system.

The PAC system may be installed onto an existing centrifuge 20, and may be located near a feed pipe of the centrifuge 20. In some embodiments, the PAC system is configured for use with an HF inverting filter centrifuge, such as the Heinkel HF inverting filter centrifuge previously mentioned in this disclosure. In many embodiments, the PAC system injects pressurized gas, such as nitrogen or air, through the feed pipe into the bowl of the centrifuge 20 (in the case of a solid bowl centrifuge) while the centrifuge 20 is spinning. Gas injection may occur anytime after the centrifuge 20 is full, and may occur before or after the final spin cycle. In some embodiments, the injected gas is pressurized to 40 psi. Alternatively, the gas may be at a pressure of up to 90 psi. In many embodiments, the PAC system operates at ambient temperature. Alternatively, the PAC system may heat the gas prior to injection in order to achieve a vaporizing effect on residual moisture in the CBD isolate in the centrifuge. When heated, the temperature may reach about 95° C. to 120° C., depending on what can be withstood by the centrifuge materials. The temperature range may also depend on what is appropriate and safe for the sample materials inside the centrifuge, particularly in cases where the solid, not the liquid, is the desired result (i.e. in the case of CBD isolate production). In many embodiments, the PAC system is installed onto the centrifuge 20 and engaged when necessary. This allows the PAC system to remain on a centrifuge even when standard centrifugation, without PAC, is sufficient for a particular centrifugation process.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

Although certain embodiments and examples are disclosed above, inventive subject matter extends beyond the specifically disclosed embodiments to other alternative embodiments and/or uses, and to modifications and equivalents thereof. Thus, the scope of the claims appended hereto is not limited by any of the particular embodiments described above. The structures, systems, methods, and/or devices described herein may be embodied as integrated components or as separate components. Furthermore, various omissions, substitutions, and changes in the form of the methods and systems described herein may be made without departing from the spirit of the inventions disclosed herein.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy. Furthermore, the phrase "at least one of" may be used as a shorthand way of saying "and/or". In this regard, the phrase "at least one of" may mean the same thing as "and/or".

The term "about" is used to mean approximately, and is not intended as a limiting term. For example, the disclosure includes the phrase "the wash solvent 32 is a cold solvent and defines a temperature that is less than or equal to about −10 degrees C." and in this context, "about" is not intended to limit the temperature to exactly −10 degrees C. In this regard, the phrase "the wash solvent 32 is a cold solvent and defines a temperature that is less than or equal to about −10 degrees C." may be interpreted to mean that the temperature ranges between +/−5 degrees of the stated value, or −15 degrees C. to −5 degrees C. With respect to time, the term "about" may be intended to mean+/−5 minutes.

The term "continuous" is used to encompass continuous, semi-continuous, quasi-continuous, and/or batch processing methods. For example, the disclosure includes the phrase "methods for the continuous production of cannabidiol (CBD) isolate" and in this context, "continuous" is meant to include the possibility of a continuous, semi-continuous, quasi-continuous, and/or batch method.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A method of producing cannabidiol (CBD) isolate, comprising:
    dissolving, via a first agitated vessel, a first CBD oil in a first solvent to thereby form a first slurry comprising a first CBD isolate and a first excess solvent;
    sending at least a portion of the first slurry from the first agitated vessel to a centrifuge;
    separating, via the centrifuge, at least a first portion of the first CBD isolate from the first excess solvent to thereby form a first separated batch;
    sending at least a portion of the first separated batch to a first dryer; and
    drying, via the first dryer, at least a second portion of the first CBD isolate from the at least the portion of the first separated batch.

2. The method of claim 1, further comprising heating, via a jacket of the first agitated vessel, the first slurry to reach a dissolving temperature whereby the first CBD oil dissolves in the first solvent.

3. The method of claim 1, further comprising cooling, via a jacket of the first agitated vessel, the first slurry to reach a crystallization temperature whereby CBD crystals precipitate.

4. The method of claim 1, further comprising agitating, via the first agitated vessel, the first slurry.

5. The method of claim 1, wherein the first solvent comprises at least one of pentane and heptane.

6. The method of claim 1, wherein the centrifuge comprises at least one of a filtering centrifuge and a solid bowl centrifuge.

7. The method of claim 1, further comprising washing the at least the first portion of the first CBD isolate with a wash solvent, wherein the washing occurs at least partially during the separating.

8. The method of claim 7, further comprising:
    after the washing, collecting excess wash solvent; and
    after the washing, drying, via the first dryer, the at least the first portion of the first CBD isolate.

9. The method of claim 1, further comprising collecting the at least the first portion of the first CBD isolate in a first collection vessel coupled to the first dryer.

10. The method of claim 1, further comprising:
    dissolving, via the first agitated vessel, a second CBD oil in a second solvent to thereby form a second slurry comprising a second CBD isolate and a second excess solvent;
    after separating at least the first portion of the first CBD isolate from the first excess solvent, sending at least a portion of the second slurry from the first agitated vessel to the centrifuge;
    then, separating, via the centrifuge, at least a first portion of the second CBD isolate from the second excess solvent to thereby form a second separated batch;
    then, sending at least a portion of the second separated batch to the first dryer; and
    then, drying, via the first dryer, at least a second portion of the second CBD isolate from the at least the portion of the second separated batch.

11. The method of claim 1, further comprising:
    dissolving, via the first agitated vessel, a second CBD oil in a second solvent to thereby form a second slurry comprising a second CBD isolate and a second excess solvent;
    after separating at least the first portion of the first CBD isolate from the first excess solvent, sending at least a portion of the second slurry from the first agitated vessel to the centrifuge;
    then, separating, via the centrifuge, at least a first portion of the second CBD isolate from the second excess solvent to thereby form a second separated batch;
    then, sending at least a portion of the second separated batch to a second dryer; and
    then, drying, via the second dryer, at least a second portion of the second CBD isolate from the at least the portion of the second separated batch.

12. The method of claim 11, wherein drying, via the first dryer, at least the second portion of the first CBD isolate occurs at least partially during dissolving the second CBD oil in the second solvent and separating at least the first portion of the second CBD isolate from the second excess solvent.

13. The method of claim 1, further comprising:
    dissolving, via a second agitated vessel, a second CBD oil in a second solvent to thereby form a second slurry comprising a second CBD isolate and a second excess solvent;
    after separating at least the first portion of the first CBD isolate from the first excess solvent, sending at least a portion of the second slurry from the second agitated vessel to the centrifuge;
    then, separating, via the centrifuge, at least a first portion of the second CBD isolate from the second excess solvent to thereby form a second separated batch;
    then, sending at least a portion of the second separated batch to the first dryer; and
    then, drying, via the first dryer, at least a second portion of the second CBD isolate from the at least the portion of the second separated batch.

14. The method of claim 13, wherein drying, via the first dryer, at least the second portion of the first CBD isolate occurs at least partially during dissolving the second CBD oil in the second solvent and separating at least the first portion of the second CBD isolate from the second excess solvent.

15. The method of claim 1, further comprising:
    dissolving, via a second agitated vessel, a second CBD oil in a second solvent to thereby form a second slurry comprising a second CBD isolate and a second excess solvent;

after separating at least the first portion of the first CBD isolate from the first excess solvent, sending at least a portion of the second slurry from the second agitated vessel to the centrifuge;

then, separating, via the centrifuge, at least a first portion of the second CBD isolate from the second excess solvent to thereby form a second separated batch;

then, sending at least a portion of the second separated batch to a second dryer; and then, drying, via the second dryer, at least a second portion of the second CBD isolate from the at least the portion of the second separated batch.

16. The method of claim 15, wherein drying, via the first dryer, at least the second portion of the first CBD isolate occurs at least partially during sending at least the portion of the second separated batch to the second dryer.

17. The method of claim 15, further comprising:

dissolving, via the first agitated vessel, a third CBD oil in a third solvent to thereby form a third slurry comprising a third CBD isolate and a third excess solvent;

after separating at least the first portion of the second CBD isolate from the second excess solvent, sending at least a portion of the third slurry from the first agitated vessel to the centrifuge;

then, separating, via the centrifuge, at least a first portion of the third CBD isolate from the third excess solvent to thereby form a third separated batch;

then, sending at least a portion of the third separated batch to the second dryer; and then, drying, via the second dryer, at least a second portion of the third CBD isolate from the at least the portion of the third separated batch.

18. The method of claim 17, wherein dissolving the third CBD oil in the third solvent occurs at least partially during drying, via the second dryer, at least the second portion of the second CBD isolate.

19. The method of claim 15, further comprising:

dissolving, via a third agitated vessel, a third CBD oil in a third solvent to thereby form a third slurry comprising a third CBD isolate and a third excess solvent;

after separating at least the first portion of the second CBD isolate from the second excess solvent, sending at least a portion of the third slurry from the third agitated vessel to the centrifuge;

then, separating, via the centrifuge, at least a first portion of the third CBD isolate from the third excess solvent to thereby form a third separated batch;

then, sending at least a portion of the third separated batch to the second dryer; and then, drying, via the second dryer, at least a second portion of the third CBD isolate from the at least the portion of the third separated batch.

20. The method of claim 15, further comprising:

dissolving, via the first agitated vessel, a third CBD oil in a third solvent to thereby form a third slurry comprising a third CBD isolate and a third excess solvent;

after separating at least the first portion of the second CBD isolate from the second excess solvent, sending at least a portion of the third slurry from the first agitated vessel to the centrifuge;

then, separating, via the centrifuge, at least a first portion of the third CBD isolate from the third excess solvent to thereby form a third separated batch;

then, sending at least a portion of the third separated batch to a third dryer; and then, drying, via the third dryer, at least a second portion of the third CBD isolate from the at least the portion of the third separated batch.

\* \* \* \* \*